US011096388B2

(12) United States Patent
Paun et al.

(10) Patent No.: US 11,096,388 B2
(45) Date of Patent: Aug. 24, 2021

(54) PERFUSION BIOREACTOR, PERFUSION DEVICE, ARTIFICIAL LIVER SYSTEM, AND RELATED METHODS

(71) Applicant: MORPHOCELL TECHNOLOGIES INC., Lac-Brome (CA)

(72) Inventors: Radu Alexandru Paun, L'Ile Perrot (CA); Shawana Habib, Montréal (CA); Massimiliano Paganelli, Outremont (CA); Claudia Raggi, Outremont (CA)

(73) Assignee: MORPHOCELL TECHNOLOGIES INC., Montreal (CA)

( * ) Notice: Subject to any disclaimer, the term of this patent is extended or adjusted under 35 U.S.C. 154(b) by 0 days.

(21) Appl. No.: 17/057,061

(22) PCT Filed: May 22, 2019

(86) PCT No.: PCT/CA2019/050698
§ 371 (c)(1),
(2) Date: Nov. 19, 2020

(87) PCT Pub. No.: WO2019/222847
PCT Pub. Date: Nov. 28, 2019

(65) Prior Publication Data
US 2021/0176984 A1 Jun. 17, 2021

Related U.S. Application Data

(60) Provisional application No. 62/674,696, filed on May 22, 2018.

(51) Int. Cl.
*A01N 1/02* (2006.01)
*C12N 5/071* (2010.01)
(Continued)

(52) U.S. Cl.
CPC .......... *A01N 1/0247* (2013.01); *A01N 1/021* (2013.01); *C12M 21/08* (2013.01); *C12M 25/02* (2013.01);
(Continued)

(58) Field of Classification Search
CPC ........ A01N 1/0247; A01N 1/021; A01N 1/02; A01N 1/0205; A01N 1/0263;
(Continued)

(56) References Cited

U.S. PATENT DOCUMENTS

2015/0004077 A1* 1/2015 Wikswo ................. C12M 35/08
422/502
2016/0083685 A1* 3/2016 Niazi ....................... C07K 1/22
435/69.1

FOREIGN PATENT DOCUMENTS

CN 201064500 5/2008
CN 201211251 3/2009
(Continued)

OTHER PUBLICATIONS

International Search Report and Written Opinion of the Office of Earlier Examination (Canadian Intellectual Property Office) dated Jul. 26, 2019 for PCT application PCT/CA2019/050698.
(Continued)

*Primary Examiner* — Michael L Hobbs
(74) *Attorney, Agent, or Firm* — Norton Rose Fulbright Canada LLP (57) ABSTRACT

A perfusion bioreactor and a perfusion device. Each perfusion device has a mesh structure, and an encapsulated organ tissue (EOT) disposed in the mesh structure. The EOT has a body with a thickness defined between a first surface of the body and a second surface of the body. The body has at least one channel extending into the body from one of the first and second surfaces to receive a fluid therein. The at least one
(Continued)

channel has a diameter selected to diffuse solutes out of the fluid and into the body. The perfusion devices are arranged one adjacent to another and spaced apart from each other along the length of the bioreactor to receive fluid, and to perfuse the fluid to the EOT of each perfusion device and to the at least one channel therein. A method of processing blood plasma and an artificial liver system are also disclosed.

27 Claims, 9 Drawing Sheets

(51) Int. Cl.
    *C12M 3/00*     (2006.01)
    *C12M 1/26*     (2006.01)
    *C12M 1/00*     (2006.01)
    *C12M 1/12*     (2006.01)
(52) U.S. Cl.
    CPC ............ *C12M 29/04* (2013.01); *C12M 29/10* (2013.01); *C12M 29/24* (2013.01); *C12M 33/14* (2013.01); *C12N 5/0697* (2013.01)
(58) Field of Classification Search
    CPC ...... C12M 21/08; C12M 29/10; C12M 29/04; C12M 29/24; C12M 25/02; C12M 33/14; C12N 5/0697
    See application file for complete search history.

(56) References Cited

FOREIGN PATENT DOCUMENTS

| | | |
|---|---|---|
| CN | 201418905 | 3/2010 |
| WO | 2018094522 | 5/2018 |

OTHER PUBLICATIONS

Ijima et al. "Development of a hybrid artificial liver using a polyurethane foam/hepatocyte-spheroid packed-bed module". The International Journal of Artificial Organs. 2000, vol. 23(6). pp. 389-397. ISSN 0391-3988.
Lu et al. "A new fluidized bed bioreactor based on diversion-type microcapsule suspension for bioartificial liver systems". PLoS One Feb. 3, 2016 (Mar. 22, 2016), vol. 11(2), ISSN 1932-6203.
Xia et al. "Hepatocyte function within a stacked double sandwich culture plate cylindrical bioreactor for bioartificial liver system". Biomaterials 2012, vol. 33. pp. 7925-7932. ISSN 0142-9612.
Park and Lee. "Bioartificial liver systems: current status and future perspective". J. Biosci. Bioeng. Apr. 1, 2005 (Apr. 1, 2005) vol. 99(4). pp. 311-319. ISSN 1389-1723.
Zhang et al. "A decade of progress in liver regenerative medicine". Biomaterials 2018 vol. 157. pp. 161-176. ISSN 0142-9612.
Allen et al. "Advances in bioartificial liver devices". Hepatology, Sep. 2001 vol. 34(3). pp. 447-455. ISSN 0270-9139.
Banares et al. "Liver support systems: will they ever reach prime time?". Curr. Gastroenterolo. Rep, Mar. 2013; vol. 15(3). pp. 312. ISSN 1522-8037.
Faenza et al, "MARS and Prometheus: Our Clinical Experience in Acute Chronic Liver Failure", Transplantation Proceedings, 40, 1169-1171 (2008).
Tsang et al, "Fabrication of 3D hepatic tissues by additive photopatterning of cellular hydrogels", The FASEB Journal—Research Communication, pp. 790-801.
Saliba et al, "Albumin Dialysis With a Noncell Artificial Liver Support Device in Patients With Acute Liver Failure", American College of Physicians, Annals of Internal Medicine, 2013; 159:522-531.
Bernal et al. "Acute Liver Failure", The New England Journal of Medicine, 2013; 369:2525-34.
Park et al, "Bioartificial Liver Systems: Current Status and Future Perspective" Journal of Bioscience and Bioengineering, vol. 99, No. 4, 311-319. 2005.
McMurtrey, "Roles of Diffusion Dynamics in Stem Cell Signaling and Three-Dimensional Tissue Development", Institute of Neural Regeneration & Tissue Engineering, Stem Cells and Development, vol. 26, No. 18, 2017.
Jalan et al "Prospects for Extracorporeal Liver Support" Recent Advances in Clinical Ractice, Gut 2004;53:890-898.
Demetriou et al "Prospective, Randomized, Multicenter, Controlled Trial of a Bioartificial Liver in Treating Acute Liver Failure" Annals of Surgery, vol. 239, No. 5, May 2004.
Khuroo et al "Molecular Adsorbent Recirculating System for Acute and Acute-on-Chronic Liver Failure: A Meta-analysis", Liver Transplantation, vol. 10, No. 9 Sep. 2004: pp. 1099-1106.
Lee et al, "Development of 3D Microvascular Networks Within Gelatin Hydrogels Using Thermoresponsive Sacrificial—Microfibers" Advanced Healthcare Materials, 2016, 5, 781-785.
"An Assessment of Liver Disease in Canada" Canadian Liver Foundation National Office, Mar. 2013.
Miller et al, "Rapid casting of patterned vascular networks for perfusable engineered three-dimensional tissues", Nature Materials, Advance Online Publication, Published Online: Jul. 1, 2012 | DOI: 10.1038/NMAT3357.
Habka, et al "Future Economics of Liver Transplantation: A 20-Year Cost Modeling Forecast and the Prospect of Bioengineering Autologous Liver Grafts", PLoS ONE 10(7): e0131764. doi:10.1371/journal.pone.0131764.
Aggarwal, S. , Obrist, W. , Yonas, H. , Kramer, D. , Kang, Y. , Scott, V. and Planinsic, R. (2005), Cerebral hemodynamic and metabolic profiles in fulminant hepatic failure: Relationship to outcome. Liver Transpl, 11: 1353-1360. doi:10.1002/lt.20479.
Bower, William A., et al. (2007), Population-Based Surveillance for Acute Liver Failure. The American Journal of Gastroenterology, vol. 102, No. 11: 2459-2463. doi:10.1111/j.1572-0241.2007.01388.x.
Escorsell, Angels, et al. (2007), Acute Liver Failure in Spain: Analysis of 267 Cases. Liver Transplantation, vol. 13, No. 10: 1389-1395. doi:10.1002/lt.21119.
Dethloff, T., Tofteng, F., Frederiksen, H.-J., Hojskov, M., Hansen, B. A., & Larsen, F. S. (2008), Effect of Prometheus liver assist system on systemic hemodynamics in patients with cirrhosis: A randomized controlled study. World Journal of Gastroenterology: WJG, vol. 14, No. 13: 2065-2071. doi:10.3748/wjg.14.2065.
Ellis, A J, et al. (1996), Pilot-Controlled Trial of the Extracorporeal Liver Assist Device in Acute Liver Failure. Hepatology, vol. 24, No. 6: 1446-1451. doi:10.1002/hep.510240625.
QuickStats: Death Rates for Chronic Liver Disease and Cirrhosis, by Sex and Age Group—National Vital Statistics System, United States, 2000 and 2015. MMWR Morb Mortal Wkly Rep 2017;66:1031. DOI: http://dx.doi.org/10.15585/mmwr.mm6638a9.
Mendizabal M, Silva MO. Liver transplantation in acute liver failure: A challenging scenario. World Journal of Gastroenterology. 2016;22(4):1523-1531. doi:10.3748/wjg.v22.i4.1523.

\* cited by examiner

PERFUSION BIOREACTOR, PERFUSION DEVICE, ARTIFICIAL LIVER SYSTEM, AND RELATED METHODS

CROSS-REFERENCE TO RELATED APPLICATIONS

This application is a national phase entry under 35 U.S.C. 371 of PCT application PCT/CA2019/050698 filed May 22, 2019, which claims priority to US provisional patent application No. 62/674,696 filed May 22, 2018, the entire contents of both of which are incorporated by reference herein.

TECHNICAL FIELD

The application relates generally to organ replacement therapy and, more particularly, to reactors, devices, and systems for performing same.

BACKGROUND

Acute liver failure (ALF) is characterized by an abrupt decrease in hepatic function following a severe insult to the liver in patients with no pre-existing liver disease. A standard treatment for acute liver failure is liver transplantation, which should be carried out within a few days from the onset of symptoms to avoid the progression to multi-organ failure. Liver transplantation is difficult, risky and not widely available. The liver's regenerative abilities are well documented in the literature. Since patients with ALF often do not have any underlying disease prior to the injury, approximatively 80% of transplants might be avoided if liver function could be replaced for the time needed for the liver to regenerate, such as with an extracorporeal system.

Some extracorporeal systems to treat liver failure are cell-free liver support systems, which are based on molecular adsorption and albumin dialysis to purify the blood. The systems are usually used in conjunction with hemodialysis to remove water soluble solutes. However, clinical trials have shown no significant differences in patient survival between standard therapy and some approved extracorporeal systems.

Some cell-based dialysis systems are under investigation. The use of human liver cells is favored since it circumvents unwanted effects associated with the use of xenogeneic liver cells. However, human liver cells are limited in availability, difficult to culture and some have shown rapid decrease in liver specific functions with time. Another limitation of some of the devices is the limited mass exchange between the patient's blood and the extracorporeal liver cells.

SUMMARY

There is provided a perfusion bioreactor, comprising: a housing having a length defined between a housing inlet and a housing outlet, the housing having an inner surface delimiting an internal cavity of the housing disposed between the housing inlet and the housing outlet and in fluid communication therewith; and perfusion devices disposed in the internal cavity of the housing, each of the perfusion devices comprising: a mesh structure supported from the inner surface of the housing, the mesh structure having a first wall spaced apart from a second wall to define an internal mesh cavity, each of the first and second walls of the mesh structure having openings therein to permit fluid communication through the mesh structure; and an encapsulated organ tissue disposed in the internal mesh cavity between the first and second walls of the mesh structure, the encapsulated organ tissue having at least one organoid at least partially covered with a biocompatible cross-linked polymer, the encapsulated organ tissue having a body with a thickness defined between a first surface of the body adjacent the first wall of the mesh structure and a second surface of the body adjacent the second wall of the mesh structure, the body having at least one channel extending into the body from one of the first and second surfaces to receive a fluid therein, the at least one channel having a diameter selected to diffuse solutes out of the fluid and into the body; the perfusion devices being disposed in the internal cavity of the housing one adjacent to another and spaced apart from each other along the length of the housing to receive the fluid conveyed from the housing inlet to the housing outlet, and to perfuse the fluid to the encapsulated organ tissue of each perfusion device and to the at least one channel therein.

There is provided a perfusion device, comprising: a mesh structure having a first wall spaced apart from a second wall to define an internal mesh cavity, each of the first and second walls of the mesh structure having openings therein to permit fluid communication through the mesh structure; and an encapsulated organ tissue disposed in the internal mesh cavity between the first and second walls of the mesh structure, the encapsulated organ tissue having at least one organoid at least partially covered with a biocompatible cross-linked polymer, the encapsulated organ tissue having a body with a thickness defined between a first surface of the body adjacent the first wall of the mesh structure and a second surface of the body adjacent the second wall of the mesh structure, the body having at least one channel extending into the body from one of the first and second surfaces to receive a fluid therein, the at least one channel having a diameter selected to diffuse solutes out of the fluid and into the body.

There is provided an artificial liver system, comprising: a fluid network and a pump to circulate plasma through the fluid network; and a perfusion bioreactor in fluid communication with the fluid network to receive the plasma therefrom, the perfusion bioreactor comprising: a housing having a length defined between a housing inlet and a housing outlet, the housing having an inner surface delimiting an internal cavity of the housing between the housing inlet and the housing outlet and in fluid communication therewith, the housing inlet receiving the plasma; and a plurality of perfusion devices disposed in the internal cavity of the housing, each of the perfusion devices comprising: a mesh structure supported from the inner surface of the housing, the mesh structure having a first wall spaced apart from a second wall to define an internal mesh cavity, each of the first and second walls of the mesh structure having openings therein to permit fluid communication through the mesh structure; and an encapsulated liver tissue disposed in the internal mesh cavity between the first and second walls of the mesh structure, the encapsulated liver tissue having at least one liver organoid at least partially covered with a biocompatible cross-linked polymer, the encapsulated liver tissue having a body with a thickness defined between a first surface of the body adjacent the first wall of the mesh structure and a second surface of the body adjacent the second wall of the mesh structure, the body having at least one channel extending into the body from one of the first and second surfaces to receive the plasma therein, the at least one channel having a diameter selected to diffuse undesired solutes out of the plasma and into the body; the perfusion devices being disposed in the internal cavity of the housing one adjacent to another and spaced apart from each other along the length of the housing to receive the plasma conveyed from the housing inlet to the housing outlet, and to perfuse the plasma to the encapsulated liver tissue of each perfusion device and to the at least one channel therein.

There is provided a method of processing blood plasma, comprising: conveying the blood plasma to at least one channel formed in an encapsulated liver tissue having at least one liver organoid at least partially covered with a biocompatible cross-linked polymer, the at least one channel having a diameter selected to diffuse undesired solutes out of the blood plasma and into the encapsulated liver tissue.

There is provided a method of making a perfusion device, comprising: providing at least one liver organoid at least partially covered with a biocompatible cross-linked polymer, the at least one liver organoid at least partially covered with the biocompatible cross-linked polymer having a body with at least one channel extending into the body, the at least one channel having a diameter selected to diffuse solutes out of a fluid and into the body; and positioning the body within a cavity of a mesh structure to allow the fluid to enter the cavity and the at least one channel of the body, and to exit the cavity.

DESCRIPTION OF THE DRAWINGS

Reference is now made to the accompanying figures in which.

DETAILED DESCRIPTION

Figures 1A, 1B:
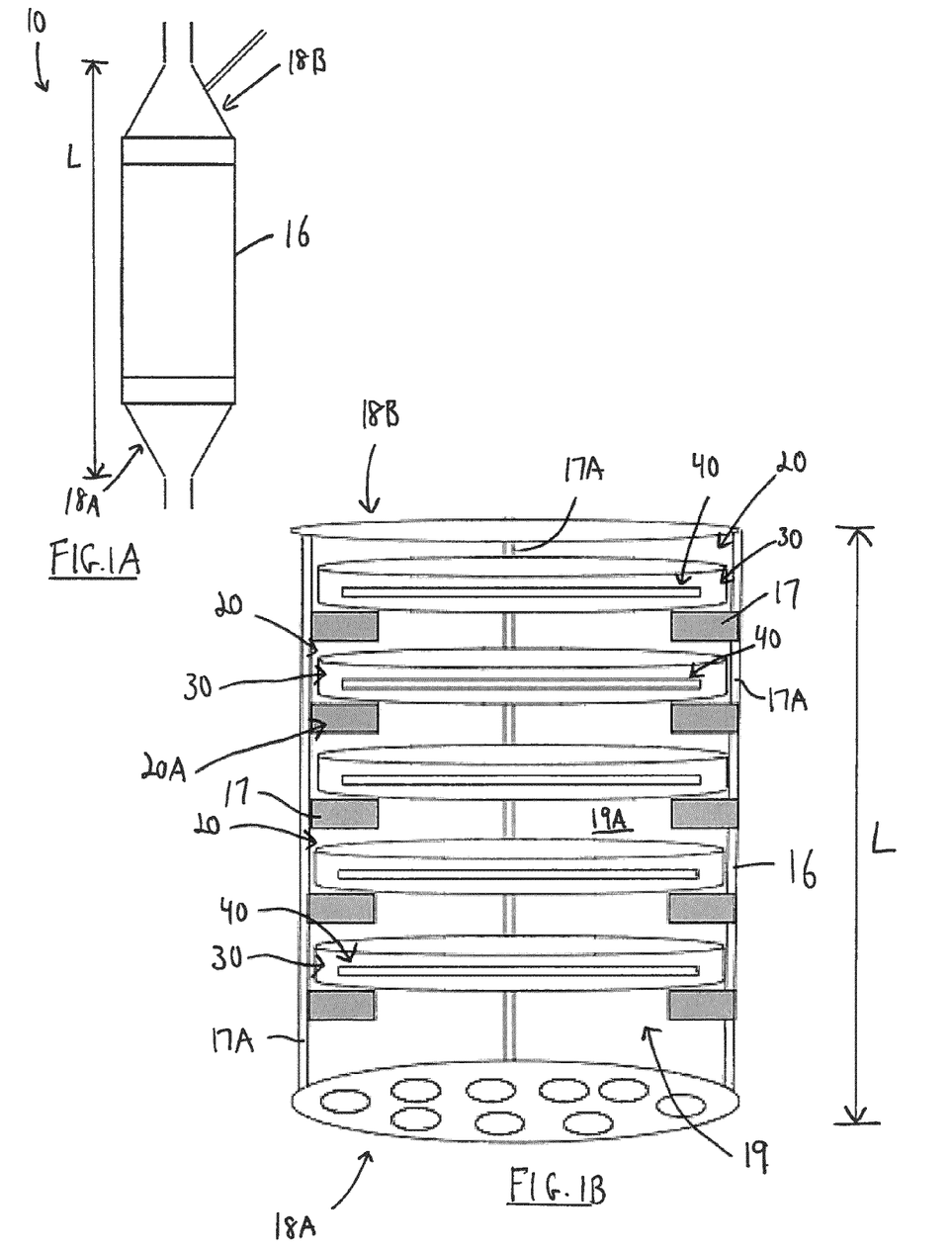
FIG. 1A is a schematic view of a perfusion bioreactor.
FIG. 1B is a schematic view of a housing and perfusion devices of the perfusion bioreactor of FIG. 1A.

FIG. 1A illustrates a perfusion bioreactor 10. The perfusion bioreactor 10 is an apparatus in which a perfusion operation is carried out. Specifically, the perfusion bioreactor 10 (sometimes referred to herein simply as the "bioreactor 10") allows for the exchange of particles between a liquid and the cells and tissues embedded within a porous biomaterial. The bioreactor 10 is a vessel having a controlled environment that allows cells to survive and perform metabolic activities. In the depicted embodiment, and as explained in more detail below, the bioreactor 10 has agglomerations of organ cells which perform at least part of the metabolic functions of an organ of the human body. The bioreactor 10 may be manufactured from any suitable biocompatible plastic, metal, or composites thereof, for example polycarbonate, in order to achieve this functionality.

In operation, the bioreactor 10 receives fluid, and conveys fluid out of the bioreactor 10. The bioreactor 10 therefore has a suitable inlet and a suitable outlet that are connected to suitable tubing. In the depicted embodiment, the bioreactor 10 has a housing 16 which is an elongated body extending a length L between a housing inlet 18A and a housing outlet 18B. The housing inlet 18A is configured to allow for infusion of plasma, nutrients, or other fluid materials into the housing 16. In the depicted embodiment, the housing 16 is a cylindrical body extending along a longitudinal axis such that it is longer than it is wide. Other shapes of the housing 16 are possible and within the scope of the present disclosure. The housing inlet and outlet 18A,18B are conical ends of the housing 16, and act as funnels to convey fluid into and out of the main portion of the housing 16. The housing 16 is hollow, and thus has an inner cavity 19 into which the fluid is conveyed for interaction with the organ cells. The inner cavity 19 is delimited by a wall of the housing, which is cylindrical in the depicted embodiment, and which defines an inner surface 19A. Fluid travels through the housing 16 by first entering the housing inlet 18A, then travelling through the inner cavity 19, and the exiting via the housing outlet 18B.

Referring to FIG. 1B, the bioreactor 10 also includes perfusion devices 20. Each perfusion device 20 performs the work of the bioreactor 10 by assisting with the exchange of particles between a liquid and the cells and tissues embedded within a porous biomaterial of each perfusion device 20. The perfusion devices 20 contain the agglomeration of organ cells which perform at least part of the metabolic functions of an organ of the human body, as explained in greater detail below. The perfusion devices 20 are disposed in the internal cavity 19 of the housing 16. As shown in FIG. 1B, the perfusion devices 20 are disposed in the internal cavity 19 one adjacent to another and spaced apart from each other along the length L of the housing 16. The perfusion devices 20 form a stack of perfusion devices 20A. In the depicted embodiment, the stack of perfusion devices 20A has an upright or vertical orientation. The perfusion devices 20 are stacked one on top of the other in the stack of perfusion devices 20A. In an alternate embodiment, the stack of perfusion devices 20A has a horizontal or inclined orientation. Irrespective of their orientation, the perfusion devices 20 and their components interact with the fluid which travels through the inner cavity 19 of the housing 16, from the housing inlet 18A to the housing outlet 18B.

Still referring to FIG. 1B, each perfusion device 20 includes a mesh structure 30 and one or more encapsulated organ tissues 40. The mesh structure 30 forms the corpus of the perfusion device 20 and provides structure thereto. The mesh structure 30 is porous, and is supported from the inner surface 19A of the housing 16 to mount each perfusion device 20 to the housing 16. The encapsulated organ tissue 40 of each perfusion device is positioned within the mesh structure 30. The mesh structure 30 is therefore any suitable device for holding the encapsulated organ tissue 40, and for allowing the fluid within the housing 16 to engage the encapsulated organ tissue 40.

Figure 11A:
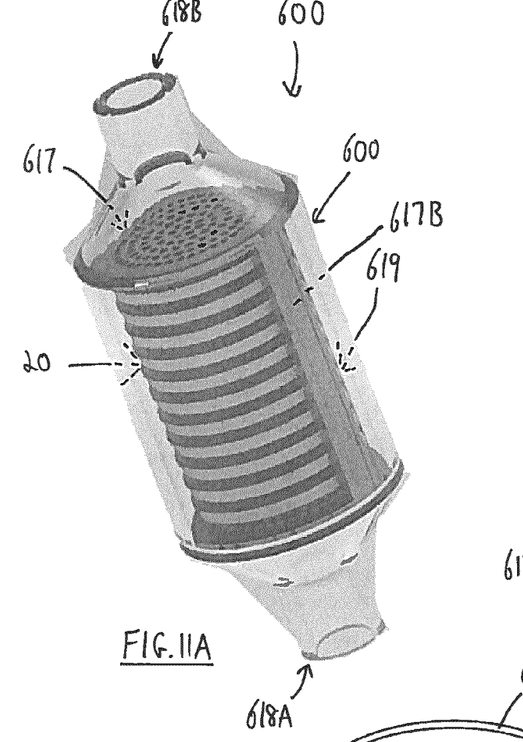
FIG. 11A is a schematic view of another perfusion bioreactor.
Figure 11B:
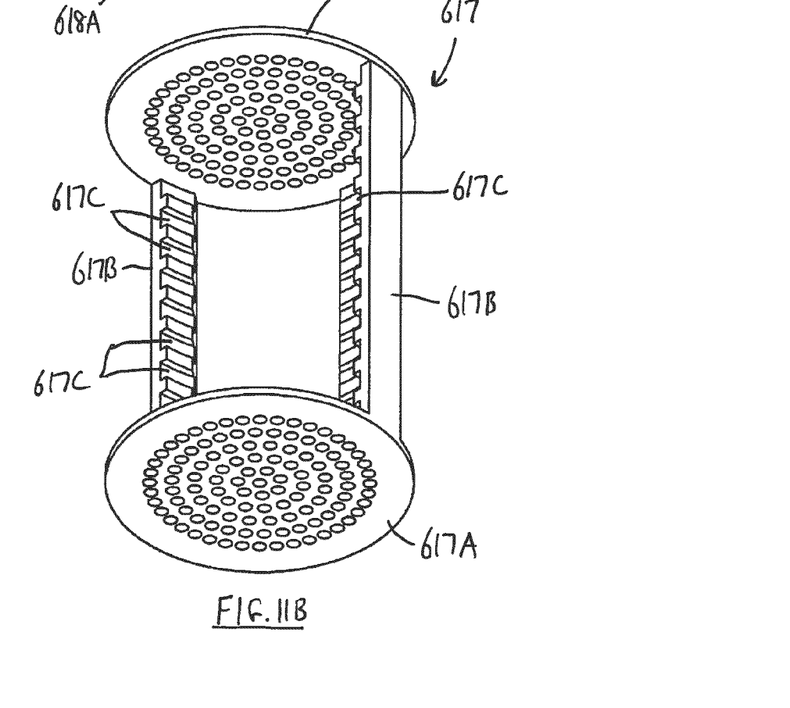
FIG. 11B is a perspective view of an internal support for the perfusion bioreactor of FIG. 11A.
Figure 11C:
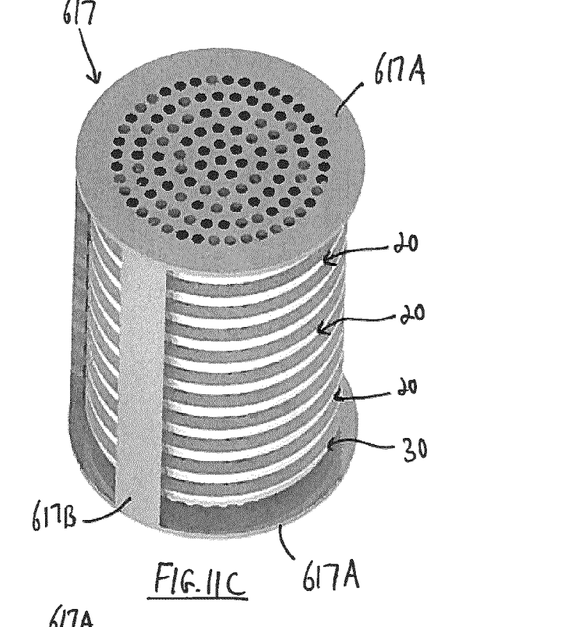
FIG. 11C is a perspective view of the internal support of FIG. 11B with perfusion devices.

Another embodiment of the bioreactor 600 is shown in FIGS. 11A to 11O. In the depicted embodiment, the bioreactor 600 has a housing 616 which is an elongated body extending a length between a housing inlet 618A and a housing outlet 618B. In the depicted embodiment, the housing 616 is a cylindrical body extending along a longitudinal axis such that it is longer than it is wide. The housing 616 is transparent and admits light. The housing inlet and outlet 618A,618B are conical ends of the housing 616, and act as funnels to convey fluid into and out of the main portion of the housing 616. The housing 616 is hollow, and thus has an inner cavity 619 into which the fluid is conveyed for interaction with the organ cells. The inner cavity 619 is delimited by a transparent wall of the housing 616, which is cylindrical in the depicted embodiment. Fluid travels through the housing 616 by first entering the housing inlet 618A, then travelling through the inner cavity 619, and the exiting via the housing outlet 618B.

Still referring to FIGS. 11A to 11O, the bioreactor 600 has an internal support 617 for supporting the perfusion devices 20. The internal support 617 is positioned within the inner cavity 619. The internal support 617 includes end plates 617A which are perforated to permit the passage of fluid therethrough. The end plates 617A are linked to each other by racks 617B which extend between the end plates 617A. The racks 617B are spaced apart from each other. The racks 617B may be attached to an internal surface of the housing 616. Each of the racks 617B includes notches or grooves 617C spaced apart along the length of the rack 617B. The mesh structure 30 of each perfusion device 20 is removably mounted to the racks 617B by being placed in the grooves 617C.

The bioreactor 10,400 provides a controlled environment. In the depicted embodiment, the internal temperature of the bioreactor 10,400 is controlled via a heat exchanger to maintain it constant at 37° C. The internal pH of the bioreactor 10,400 is controlled by modulating bicarbonate to maintain it constant at about 7.4. Since the depicted bioreactor 10,400 is used to process blood plasma, erythrocytes (i.e. red blood cells) are not present in the plasma. Therefore, an oxygen content of the plasma in the bioreactor 10,400 is controlled. The bioreactor 10,400 may be used with other types of corporeal fluids, and may control for fewer or other parameters.

The mesh structure 30 and the encapsulated organ tissues 40 are now described in greater detail.

Figure 2A:
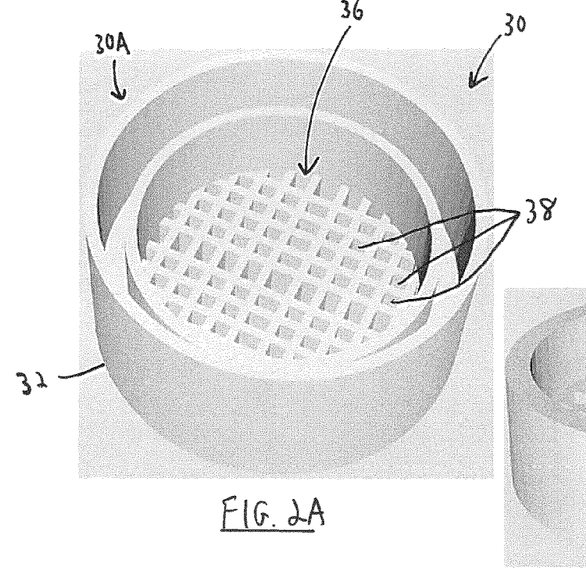
FIG. 2A is a perspective view of part of a mesh structure of the perfusion devices of FIG. 1B.
Figure 2B:
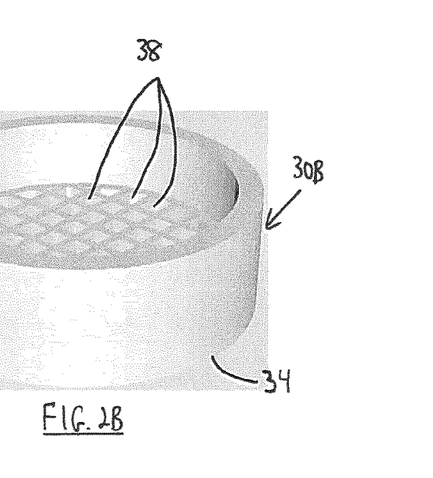
FIG. 2B is a perspective view of another part of the mesh structure of FIG. 2A.

Referring to FIGS. 2A and 2B, the mesh structure 30 has a first wall 32 spaced apart from a second wall 34 to define an internal mesh cavity 36. The encapsulated organ tissue 40 (not shown in FIGS. 2A and 2B) is disposed in the internal mesh cavity 36 between the first and second walls 32,34. The first and second walls 32,34 are porous to allow the fluid to enter the internal mesh cavity 36 to interact with the encapsulated organ tissue 40. The porous nature of the mesh structure 30 is provided by openings 38 in each of the first and second walls 32,34, which permit fluid communication through the mesh structure 30. In FIGS. 2A and 2B, the mesh structure 30 includes a base 30A and a cap 30B that is mountable on the base 30A to close the mesh structure 30 and define the internal mesh cavity 36. The base 30A includes the first wall 32 of the mesh structure 30, and the cap 30B includes the second wall 34. The cap 30B is press fit onto the base 30A.

Figure 3:
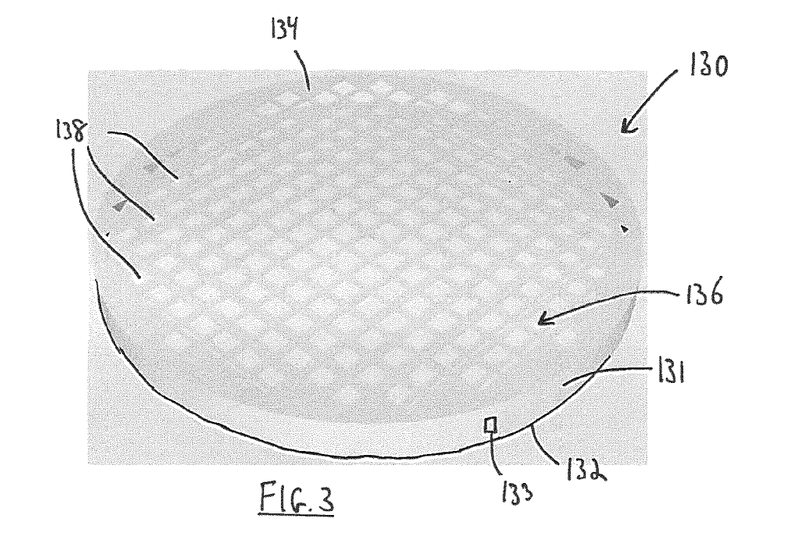
FIG. 3 is a perspective view of another mesh structure for use in the perfusion devices of FIG. 1B.

Other embodiments of the mesh structure 30 are possible. For example, FIG. 3 shows a one-piece mesh structure 130. The mesh structure 130 is cylindrical, and is shaped as a disc. The first and second walls 132,134 are shown spaced apart to define the internal mesh cavity 136. The first and second walls 132,134 also have openings 138 therein. In FIG. 3, the mesh structure 130 has a side wall 131 with an aperture 133 therein. The aperture 133 is in fluid communication with the internal mesh cavity 136. The aperture 133 allows for the introduction of components making up the encapsulated organ tissue 40 into the internal mesh cavity 136, as explained in greater detail below. Irrespective of its configuration, the mesh structure 30,130 may have a thickness between about 1 mm and about 8 mm, and may have a diameter between about 10 mm and about 80 mm. The mesh size (i.e. the size of the openings 38,138) may be between about 500 µm and about 5 mm. Although shown in FIGS. 2A-3 as being substantially circular in shape, it will be appreciated that the mesh structure 30,130 may have other shapes, including but not limited to, rectangular, square, triangular, etc.

Figure 4:
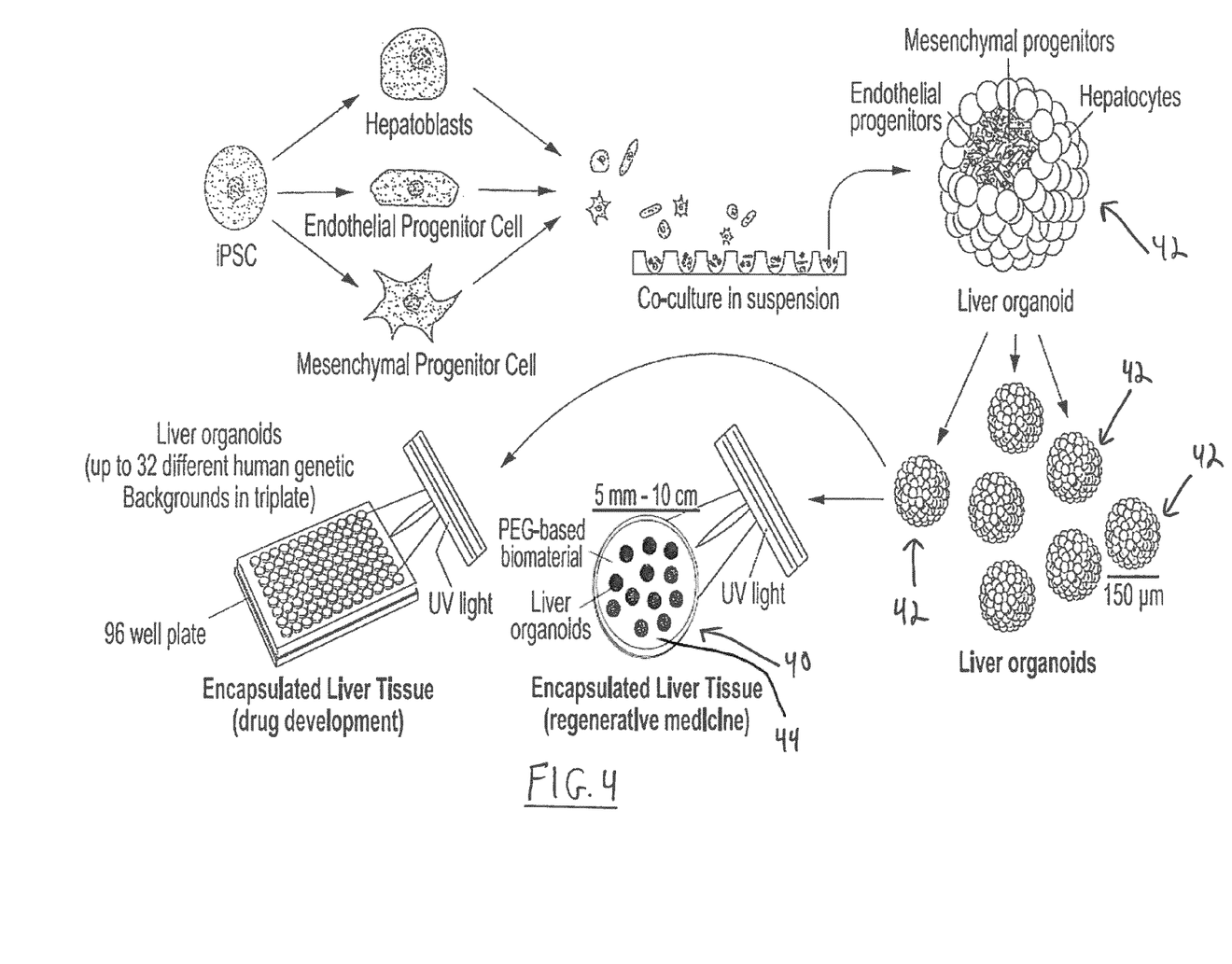
FIG. 4 shows a process for encapsulating liver organoids and making an encapsulated liver tissue for use in the perfusion devices of FIG. 1B.

Referring to FIG. 4, the encapsulated organ tissue 40 (sometimes referred to herein simply as the "EOT 40") has one or more organoids 42 that are at least partially covered with a biocompatible cross-linked polymer 44. Each organoid 42 is a grown or cultured mass of cells or tissue that resembles an organ. In FIG. 4, each organoid 42 is a liver organoid which resembles the liver, such that the EOT 40 is an encapsulated liver tissue (ELT). The fluid that enters the bioreactor 10,400 exchanges compounds with the tissue or cells of the organoids 42 within the EOT 40 so that toxic compounds are metabolized by the cells of the organoids 42 and eliminated in a non-toxic form, while useful proteins are produced by the cells of the organoids 42 and released into the fluid. Albumin, ammonia and other plasma constituents that need to be processed by the liver may therefore be metabolized by the liver organoids 42, which is similar to human liver function. The organoids 42 may also be cultured from the cells or tissues of another organ. A non-limitative list of other organs whose function can be mimicked by the organoids 42 includes the kidney, endocrine tissue, and any other tissue that can be perfused by blood and which can be agglomerated into organoids 42. It will therefore be appreciated that reference to the liver, liver organoids, or encapsulated liver tissue in the present disclosure does not limit the organoids 42 or the EOT 40 to only being formed from liver cells or tissue.

FIG. 4 shows a process to provide a plurality of monodispersed liver organoids 42 within the biocompatible and crossed-linked polymer 44. As shown, hepatoblasts, endothelial progenitor cells and mesenchymal progenitor cells are obtained from differentiating a single iPSC. The cells are mixed and co-cultured in suspension to form the liver organoid 42. In the embodiment of the liver organoid 42 shown in FIG. 4, the hepatoblasts have differentiated into hepatocytes which substantially cover a cellular core formed by mesenchymal and endothelial progenitor cells (prior to the introduction of the liver organoids 42 in the encapsulated liver tissue 40). The embodiment of the liver organoid 42 shown in FIG. 4 is substantially spherical in shape and has a relative diameter of about 150 µm. The liver organoids 42 are then encapsulated, using a cross-linking agent, which in FIG. 4 is shown as UV light, in a first compatible and cross-linkable matrix. The encapsulated liver tissue 40 can be used as transplantable liver tissue (having for example, a size between 5 mm and 10 cm) in regenerative medicine. Alternatively, the liver organoids 42 can be designed to a multiwell plate and used in drug development to determine metabolism or hepatotoxicity of screened compounds.

The polymer 44 (also referred to as a polymeric matrix) that can be used in the encapsulated liver tissue 40 forms a hydrogel around the liver organoids 42. A hydrogel refers to polymeric chains that are hydrophilic in which water is the dispersion medium. Hydrogels can be obtained from natural or synthetic polymeric networks. In the context of the present disclosure, encapsulation within the hydrogel prevents embedded liver organoids 42 from leaking out of the polymer 44. In an embodiment, each liver organoid 42 is encapsulated individually and the encapsulated liver organoids 42 can, in another embodiment, be further included in a polymeric matrix 44. In still another embodiment, the liver organoids 44 are included in a polymeric matrix 44 so as to encapsulate them. As shown in FIG. 4, the liver organoids 42 encapsulated within the hydrogel material form a disc or other cylindrical structure. Other shapes for the organoids 42 encapsulated within the hydrogel material are possible and within the scope of the present disclosure. The hydrogel may be any biocompatible material. Some non-limitative examples of hydrogels include PEG, and any polyethylene glycol (PEG) based material such as PEG-vinyl sulfone (PEG-VS).

FIG. 4 shows a process for making the encapsulated organ tissue 40, which is described in PCT patent application PCT/CA2017/051404 (published as WO 2018/094522) entitled "Encapsulated Liver Tissue" and filed Nov. 23, 2017, the entirety of which is incorporated by reference herein. The organoids 42 may be harvested from the ultra-low attachment flasks and centrifuged at low speed (400 g for 5 minutes) to form a pellet. The pellet (about 3 000 organoids) may be resuspended in 5% 4-arm PEG-vinyl sulfone (20 kDa) solution in sterile PBS without calcium and magnesium supplemented with 0.1% N-vinyl-2-pyrrilidone and 0.4 mg/mL Irgacure 2959. A 50 µL droplet of such a solution (containing about 100 organoids 42) may be generated and deposed in a well of a 96-well plate, and subsequently cross-linked under UV light (5 minutes 1090 µW/cm$^2$ at a distance of 4 cm). The generated encapsulated liver tissue 40 may be maintained in complete William's E medium/complete EMB2 (1:1) medium supplemented with, 20 ng/mL OSM and 10 µM dexamethasone for 5 days. Five days after encapsulation, the OSM supplementation may be suspended and the ratio complete William's E medium/complete EBM2 medium may be changed from 1:1 to 4:1. The tissue may be cultured at 37° C. in ambient $O_2$/5% $CO_2$ and the medium may be changed every other day. Albumin secretion may be assessed weekly in the conditioned medium. It may be possible for encapsulated organoids 42 to preserve their ability to secrete albumin through the hydrogel over more than 7 weeks of culture, proving their survival and maintenance of their differentiated status within the polymer 44 while confirming the diffusion of the secreted protein outside of it. The encapsulated liver tissue 40 may be solid enough to be manipulated with instruments without losing its shape and integrity.

Figure 5A:
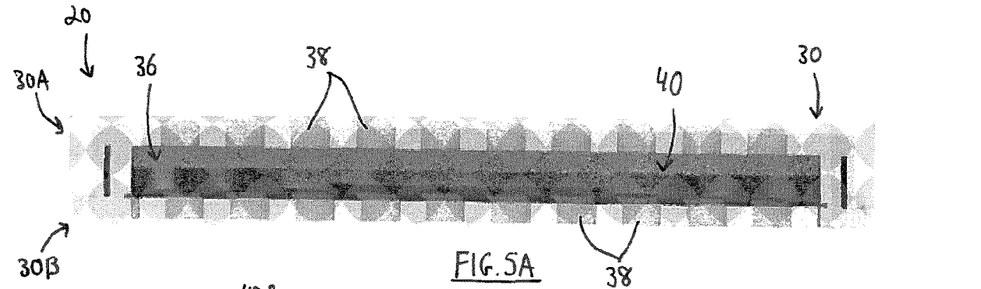
FIG. 5A is a perspective view of one of the perfusion devices of FIG. 1B.
Figures 5B, 5C, 5D:
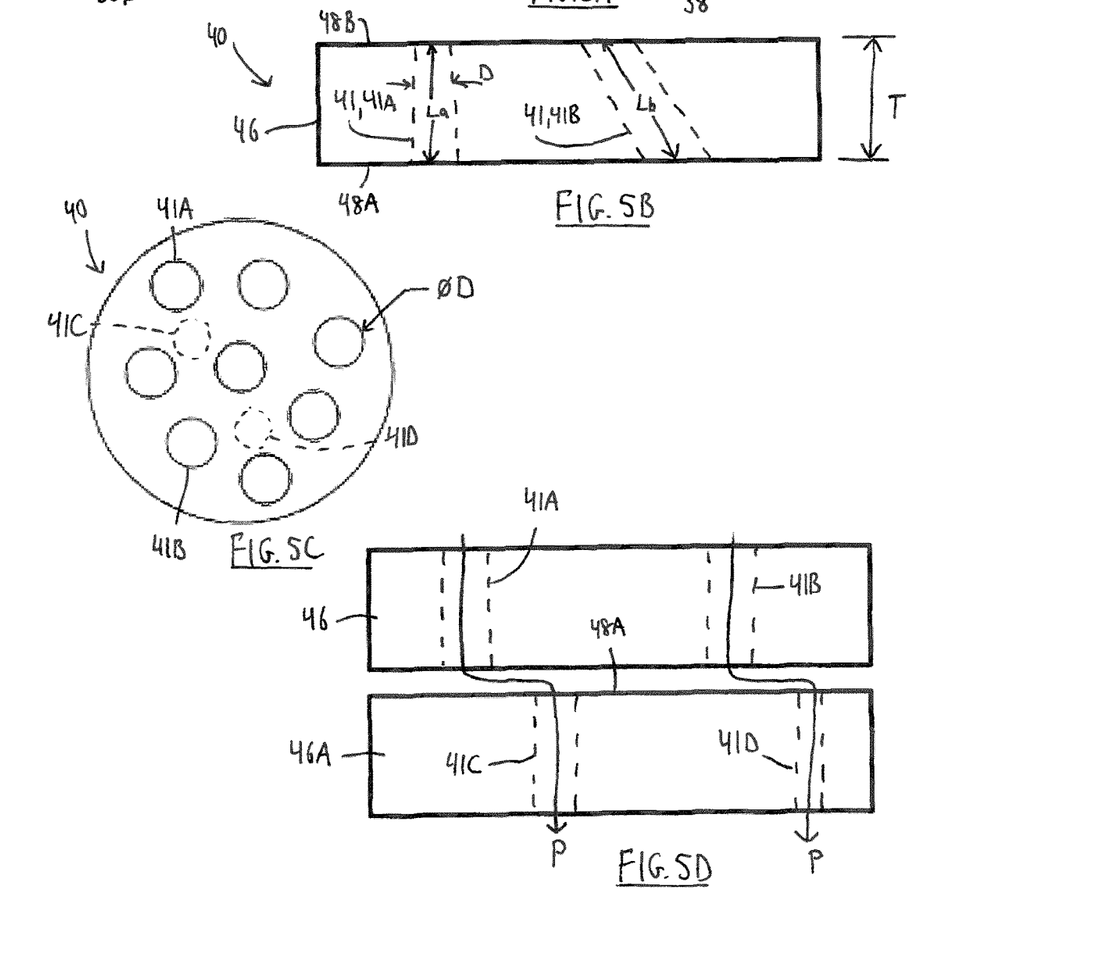
FIG. 5B is a side elevational view of an encapsulated organ tissue of the perfusion device shown in FIG. 5A.
FIG. 5C is an end view of the encapsulated organ tissue of the perfusion device shown in FIG. 5A.
FIG. 5D is a side elevational view of the encapsulated organ tissues of two of the perfusion devices of FIG. 1B arranged adjacent to each other.

FIGS. 5A to 5C show one of the perfusion devices 20 and the EOT 40. The EOT 40 has a body 46 which provides physical structure to the EOT 40. The body 46 defines a thickness T. The thickness T is defined between a first surface 48A of the body 46 adjacent to the first wall 32 of the mesh structure 30, and a second surface 48B of the body 46 adjacent to the second wall 34. The EOT 40 is therefore "sandwiched" by the mesh structure 30. In the depicted embodiment, the body 46 takes the form of the mesh structure 30, and is thus shaped as a cylinder or disc. Just like the mesh structure 30, the body 46 may have other shapes, which are part of the present disclosure. In an embodiment, the thickness T of the body 46 is between about 1 mm to about 3 mm. Other values for the thickness T of the body 46 are possible and within the scope of the present disclosure.

Referring to FIGS. 5B and 5C, the EOT 40 is a three-dimensional porous body. The EOT 40 is embedded with spatially-organized passages which are perfused with the fluid (e.g. plasma) supplied to the housing 16. As shown in FIGS. 5B and 5C, the body 46 has one or more channels 41 which extend into the body 46. Each channel 41 extends into the body 46 from one or both or the of the first and second surfaces 48A,48B in order to receive the fluid into the channel 41. Each channel 41 has a diameter D. The diameter D of each channel 41 is selected so that undesirable solutes within the fluid can be diffused out of the fluid and into the surrounding tissue of the body 46 to be metabolized. Control over the diameter D of the channels 41 may allow for improved removal of molecules of a certain size from the fluid, while allowing molecules of interest which have different sizes to remain in the fluid. The diameter D of each channel 41 in the body 46 may be the same, or may vary. In an embodiment, the diameter D of one or more of the channels 41 is between about 150 µm and about 750 µm. Other values for the diameter D of the channels 41 are possible and within the scope of the present disclosure.

It can therefore be appreciated that each EOT 40 has a vascular-like structure (i.e. the channels 41) which may assist with penetration of the fluid and its solutes within the EOT 40, and with the diffusion of solutes out of the fluid into the surrounding polymer 44 hydrogel of the body 46. This contrasts with some conventional polymerized organ tissues which do not have passages, such that the diffusion of solutes is limited to only the surface of the polymerized organ tissue.

The channels 41 may be formed using any suitable technique. Some possible techniques include photolithography, sacrificial molding, or any other suitable microfabrication technique. When using photolithography, for example, forming the channels 41 includes curing portions of the biocompatible cross-linked polymer 44 with a UV light source while the body 46 remains in the internal mesh cavity 36 of the mesh structure 30. This may include covering the body 46 with a photomask which has one or more opaque portions which correspond to the ultimate location of the channels 41. The biocompatible cross-linked polymer 44 is then cured with a UV light source applied to the photomask. The portions of the body 46 covered by the opaque portions of the photomask will remain uncured to thereby form the channels 41 in the body 46. The EOT 40 may therefore be photopolymerized within the mesh structure 30. If the channels 41 are generated while the polymer 44 is in the mesh structure 30, then the photomask used in photolithography may need to coordinate the opaque portions with the openings 38 of the mesh structure 30 to allow UV light to penetrate to the hydrogel for curing to occur.

In another embodiment of photolithography within the mesh structure 30, forming the channels 41 includes injecting the at least one liver organoid 42 and the biocompatible cross-linked polymer 44 into the internal mesh cavity 36 of the mesh structure, and then curing portions of the biocompatible cross-linked polymer 44 with a UV light source to solidify the mass. The portions of the polymer 44 which are not cured form the channels 41. One technique for achieving this result involves pipetting the hydrogel polymer 44 and the organoids 42 into the internal mesh cavity 36 via the openings 38 in the first and second walls 32,34, or via the aperture 133 (see FIGS. 2A to 3). Prior to injecting the hydrogel polymer 44 and the organoids 42, both of the first and second walls 32,34 and their openings 38 can be sealed, such as with a light-transparent seal like a glass slide. The mixture is then cured and photopolymerized within the mesh structure 30.

Other techniques for forming the channels 41 are also possible and within the scope of the present disclosure. In an alternate embodiment, the EOT 40 is added to the internal mesh cavity 36 of the mesh structure 30 after photopolymerization. In yet another embodiment, the body 46 is bio-printed, or formed using a fabricated mold containing the channels 41, or by using sacrificial molding of polymers or sugars. In yet another embodiment, the endothelial progenitor cells of the liver organoid 42 organise in a capillary or a capillary-like configuration.

The shape, orientation, and path of the channels 41 may vary, and at least some of these are now described in greater detail.

Referring to FIGS. 5B and 5C, the body 46 includes multiple channels 41. The channels 41A extend through the body 46 between the first and second surfaces 48A,48B. The channels 41A therefore communicate the fluid through the body 46. A length La of the channels 41A is substantially equal to the thickness T of the body 46. The channels 41B also extend through the body 46, and also communicate the fluid through the body 46. The length Lb of the channels 41B is greater than the thickness T of the body 46 because the channels 41B are slanted or inclined with respect to the first and second surfaces 48A,48B.

Referring to FIGS. 5C and 5D, the through channels 41A,14B allow the fluid to be communicated through the body 46 of one perfusion device 20, and to the body 46A of another, immediately adjacent perfusion device 20. The channels 41A,41B of the body 46 are offset from the channels 41C,41D of the adjacent body 46A. In the embodiment where the stack of perfusion devices 20A has an upright orientation, the offset channels 41A,41B,41C,41D of the bodies 46,46A are not vertically aligned. The channels 41A,41B,41C,41D of the bodies 46,46A do not overlap. The fluid is therefore prevented from flowing directly, in a straight or non-deviated path, between the bodies 46,46A. The offset channels 41A,41B,41C,41D therefore define a winding flow path P for the fluid, such that the fluid is deviated from a straight-line path between the bodies 46,46A. In FIG. 5D, one of the winding flow paths P allows the fluid to enter the channel 41A and flow through the body 46, and then flow along the first surface 48A of the body 46A until arriving at the channel 41C, at which point the fluid enters the channel 41C and flows through the body 46A. This deviation of the fluid from one perfusion device 20 to the next may help to increase the chance of solutes diffusing out of the fluid by delaying diffusion and giving the fluid more time to interact with the organoids 42 of the EOT 40.

Figure 6:
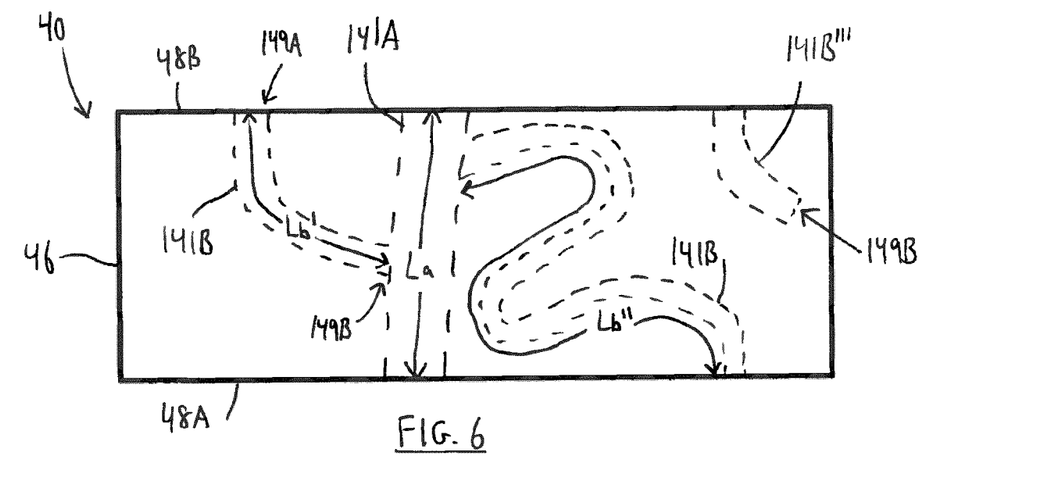
FIG. 6 is a side elevational view of another encapsulated organ tissue for use in the perfusion devices of FIG. 1B.

FIG. 6 shows another configuration of the channels 141 of the EOT 40. The channels 141 include a first or primary channel 141A and one or more other channels 141, referred to as secondary channels 141B. The primary channel 141A is a through-channel, and extends through the body 46 between the first and second surfaces 48A,48B. The secondary channels 141B extend into the body 46 from a first end 149A at one of the first and second surfaces 48A,48B, to a second end 149B within the body 46 at the primary channel 141A. The second end 149B of the secondary channels 141B opens into the primary channel 141A, such that the secondary channel 141B is in fluid communication with the primary channel 141A. The fluid may therefore be conveyed from the first or second surface 48A,48B of the body 46, through the secondary channels 141B, and into the primary channel 141A. The length La of the primary channel 141A is substantially equal to, or greater than, the thickness T of the body 46. The length Lb of the secondary channels 141B is either less than the thickness T of the body 46, or greater than the thickness T of the body 46. The length Lb' of the secondary channel 141B is less than the thickness T of the body 46. The length Lb" of the secondary channel 141B is greater than the thickness T of the body 46, such that this secondary channel 141B follows a meandering, winding, or serpentine path through the body 46. The secondary channel 141B''' is a "dead-end" channel, and extends into the body 46 from one of the first and second surfaces 48A,48B to a second end 149B within the body 46 that is not in fluid communication with any other channels 141A,141B. The dead-end secondary channel 141B''' may diffuse solvents out of the fluid and into the body 46.

Figure 7:
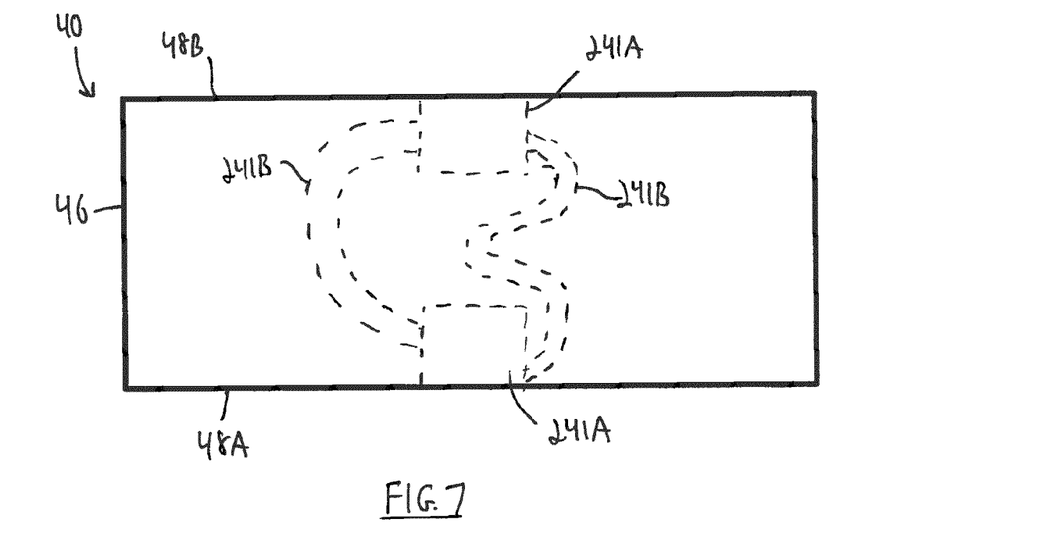
FIG. 7 is a side elevational view of another an encapsulated organ tissue for use in the perfusion devices of FIG. 1B.

FIG. 7 shows another configuration of the channels 241 of the EOT 40. The body 46 includes two primary channels 241A. Each primary channel 241A extends into the body 46 from one of the first and second surfaces 48A,48B. Each primary channel 241A is a "dead-end" channel, and does not extend through the body 46. One or more secondary channels 241B extend between the two primary channels 241A to fluidly connect them. The fluid is therefore able to pass through the body 46 from each of the first and second surfaces 48A,48B by flowing into one of the primary channels 241A, through one or more secondary channels 241B, and out the other primary channel 241A.

Referring to FIGS. 1A and 1B, the operation of the bioreactor 10 is explained in greater detail. The fluid received at the housing inlet 18A of the housing 16 is conveyed into the internal cavity 19 to perfuse the fluid to the EOT 40 of each perfusion device 20. The fluid is therefore delivered through the openings 38 in the first and second walls 32,34 of each mesh structure 30 to the organoids 42 and the channels 41 of each EOT 40. In the depicted embodiment, the fluid is conveyed against gravity, from the lower housing inlet 18A to the higher housing outlet 18B. As shown in FIG. 1B, the housing 16 has multiple supports 17 which are attached to the inner surface 19A and spaced apart along the length L of the housing 16. The mesh structure 30 of each perfusion device 20 is removably mounted to one of the supports 17. In the depicted embodiment, the supports 17 are notches or grooves in parallel columns 17A which are attached to the inner surface 19A, and which extend along the length L of the housing 16. The columns 17A are supported with sieves to prevent organoids 42 from the EOT 40 from escaping into the processed fluid leaving the fluid outlet 18B in case of tissue breakage. Other configurations for the supports 17 are possible and within the scope of the present disclosure. For example, in any alternate embodiment, each mesh structure 30 has one or more supports 17 for attaching to the inner surface 19A of the housing 16.

Still referring to FIG. 1B, the stack of perfusion devices 20A may be cryopreserved. All materials used may withstand extremely low temperatures without or with minimal fatigue. Prior to starting plasma therapy, the perfusion devices 20 may be taken out of cryopreservation and inserted into the bioreactor 10. Circulation of warm fluid (e.g. warm plasma) can thaw the organoids 42 in the bioreactor 10 and further maintain the temperature of the organoids 42 at body temperature, creating an optimal environment for the tissue. In an embodiment, between about 0.1% and about 1% of the mass of a human liver is present in the perfusion devices 20 of the housing 16. This equates to approximately from a few million to a few billion liver cells, and may also equate to between about 500 to about 10,000 organoids per perfusion device 20.

Figure 8:
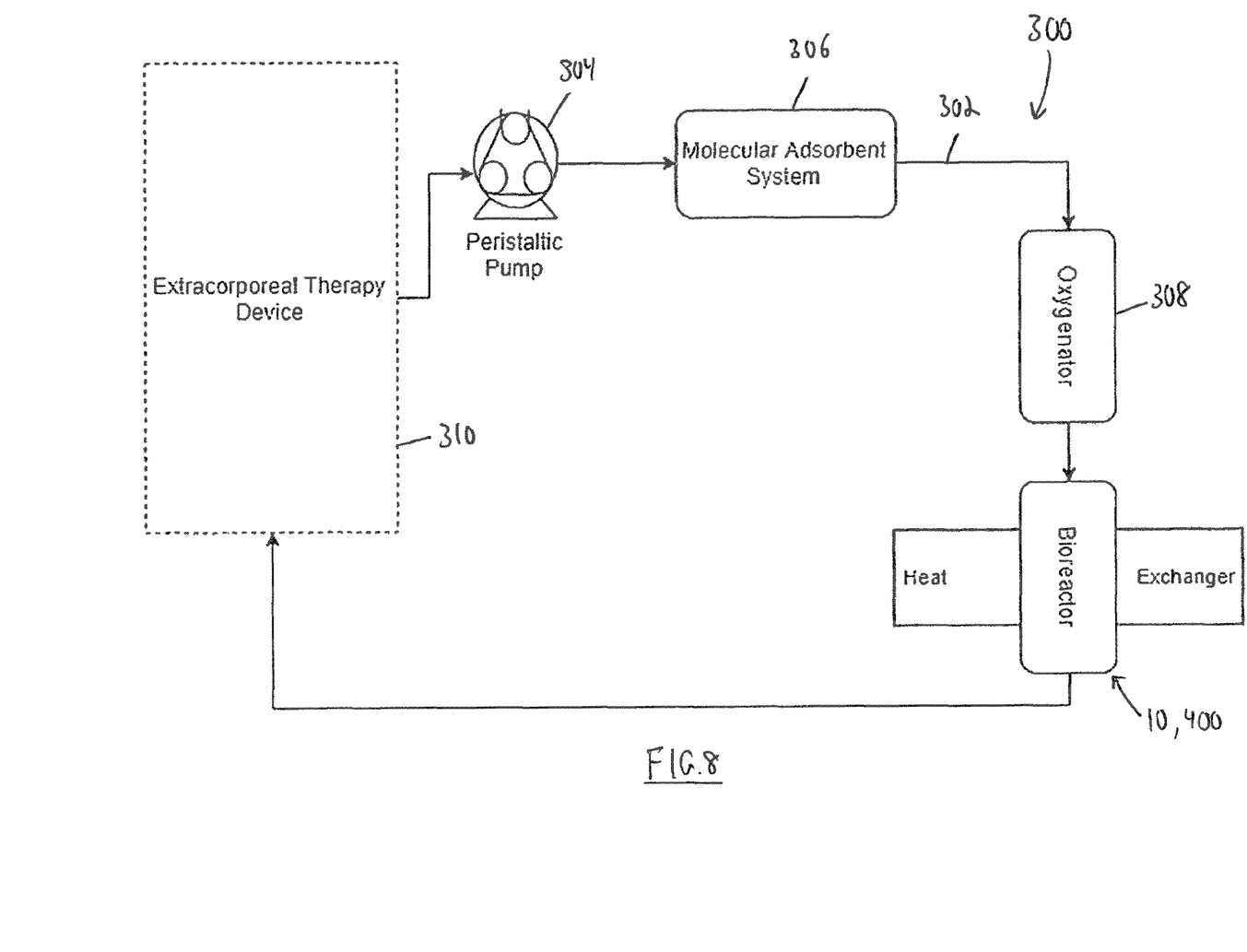
FIG. 8 is a schematic view of an artificial liver system having the perfusion bioreactor of FIG. 1A.

FIG. 8 shows an embodiment of an artificial liver system 300 having the bioreactor 10,400 described herein. The artificial liver system 300 helps to mimic the function of the human liver, and may therefore be referred to as a "Bio-Artificial Liver Device (BALD)". The artificial liver system 300 (sometimes referred to herein simply as the "system 300") includes a fluid network 302, which is a series of tubes, connectors, and other components to communicate blood plasma between the features of the system 300. The system 300 has a peristaltic pump 304 to circulate the plasma through the fluid network 302. In the depicted embodiment, the pump 304 pushes plasma through the fluid network 302 at a flow rate of between about 50 mL/min to about 300 mL/min. Infusion pumps may be placed right after the pump 304 to insert saline and/or an anticoagulant (Heparin). The fluid network 302 may have a pressure sensor to determine pressure across the system 300, and to ensure that plasma re-enters the patient at a pressure similar to that at which it was extracted.

The system 300 may optionally have an adsorbent cartridge, shown in FIG. 8 as a molecular adsorbent system 306, or MAS. The MAS 306 is any suitable perfusion device or charcoal adsorbent system. The MAS 306 is in fluid communication with the fluid network 302 to remove some of the undesired solutes from the plasma. The undesired solutes may include toxins, and high levels of bilirubin. The undesired solutes are removed from the plasma in the MAS 306 using adsorption on an activated charcoal or hydrophobic resin. The system 300 may also have an oxygenator 308 in fluid communication with the fluid network 302, as shown in FIG. 8. The oxygenator 308 operates to dissolve oxygen into the plasma to produce oxygenated plasma. The bioreactor 10,400 is shown in fluid communication with the oxygenator 308, and receives the oxygenated plasma therefrom. The oxygenated plasma enters the bioreactor 10,400 and interacts with the ELTs 40 of the perfusion devices 20, which operate to diffuse other remaining undesired solutes, not already removed by the MAS 306, out of the oxygenated plasma and into the body 46 of the EOT 40. In an alternate embodiment, the oxygenator 308 is a component of the bioreactor 10,400, and oxygenation is performed in the bioreactor 10,400 itself. In an embodiment, the system 300 is free of an oxygenator. In an embodiment, oxygenation is performed on the plasma downstream of the bioreactor 10,400. The processed plasma exiting the housing outlet 18B of the bioreactor 10,400 may be provided to attach to a commercially-available extracorporeal filtration system 310. The system 300 in FIG. 8 may therefore be an add-on device to be used with the existing extracorporeal filtration system 310. In an alternate embodiment, a dialyzer 416 (see FIG. 9) is placed in the system 300 after the bioreactor 10,400 to perform plasma dialysis.

Figure 9:
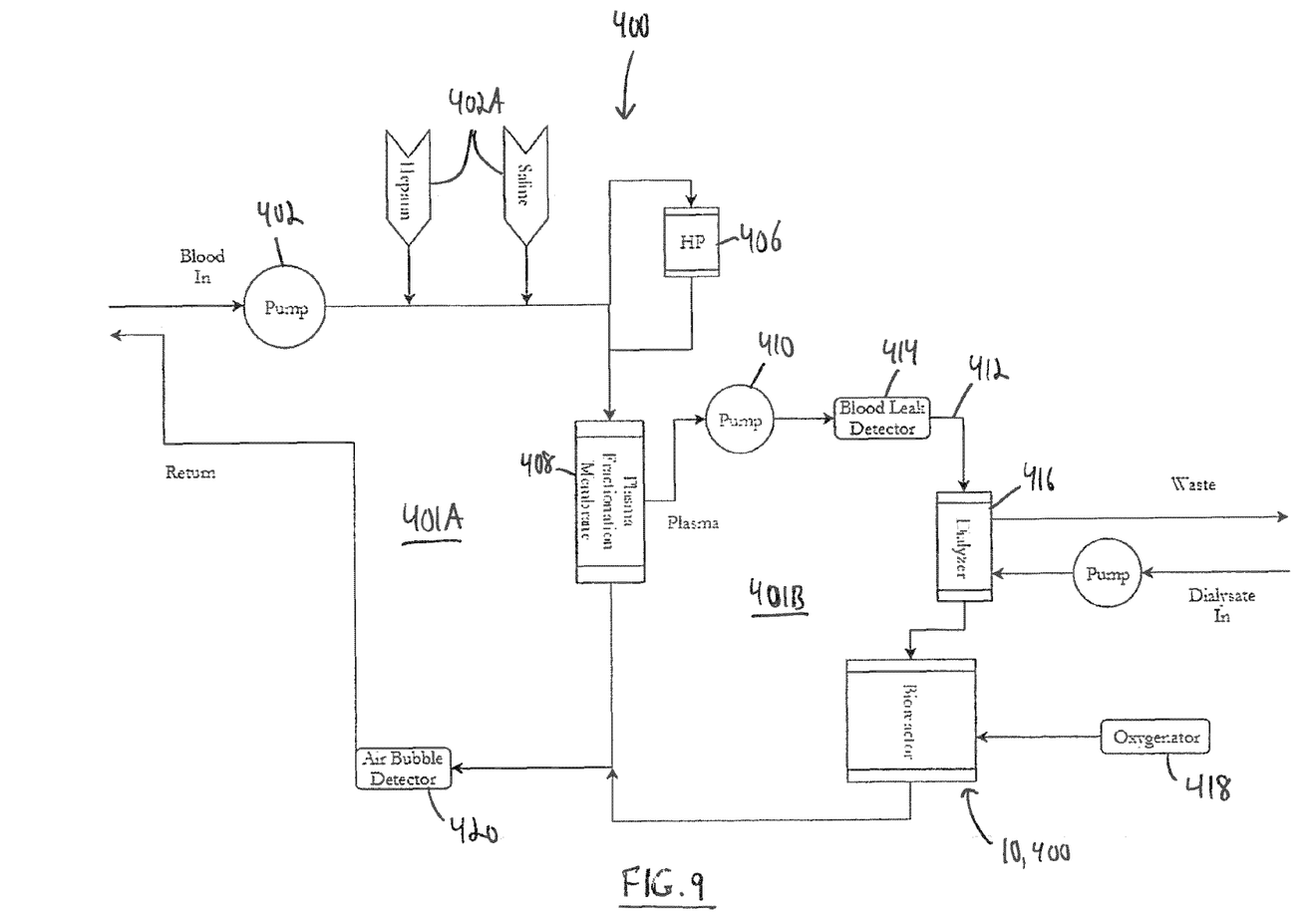
FIG. 9 is a schematic view of another artificial liver system having the perfusion bioreactor of FIG. 1A.

FIG. 9 shows another embodiment of an artificial liver system 400 having the bioreactor 10,400 described herein. The system 400 is a stand-alone extracorporeal unit which includes a blood circuit 401A and a plasma circuit 401B. The blood circuit 401A includes a pump 402 to pump blood into the system 400. Infusion pumps 402A are placed right after the pump 402 to insert saline and an anticoagulant (Heparin). In FIG. 9, the MAS 406 is positioned in the blood circuit 401A before a plasma fractionation module 408 which separates the plasma from the blood, and which provides the plasma to the plasma circuit 401B. In the plasma circuit 401B, the system 400 has a peristaltic pump 410 to circulate the plasma through the fluid network 412. A blood leak detector 414 is present before the dialyzer 416 of the plasma circuit 401B, which removes some of the undesired solutes from the plasma using a dialysate. The plasma circuit 401B also has an oxygenator 418 to dissolve oxygen into the plasma to produce oxygenated plasma. The bioreactor 10,400 is in fluid communication with the oxygenator 418, and receives the oxygenated plasma therefrom. The oxygenated plasma enters the bioreactor 10,400 and interacts with the ELTs 40 of the perfusion devices 20, which operate to diffuse other, remaining undesired solutes, not already removed by the MAS 406 or the dialyzer 416, out of the oxygenated plasma and into the bodies 46 of the EOTs 40. The processed plasma exiting the housing outlet 18B of the bioreactor 10,400 is provided back to the blood circuit 401A, where it is recombined with the separated blood products and returned to the patient's blood, or further fluid processing may be performed. The blood circuit 401A has an air bubble detector 420 to prevent air from being introduced into the blood. The system 400 may also include temperature sensor(s), flow meter(s), a cell filter(s), heat exchanger(s) to maintain a constant temperature, clamp(s), drip chamber(s), and any other suitable devices.

Figure 10:
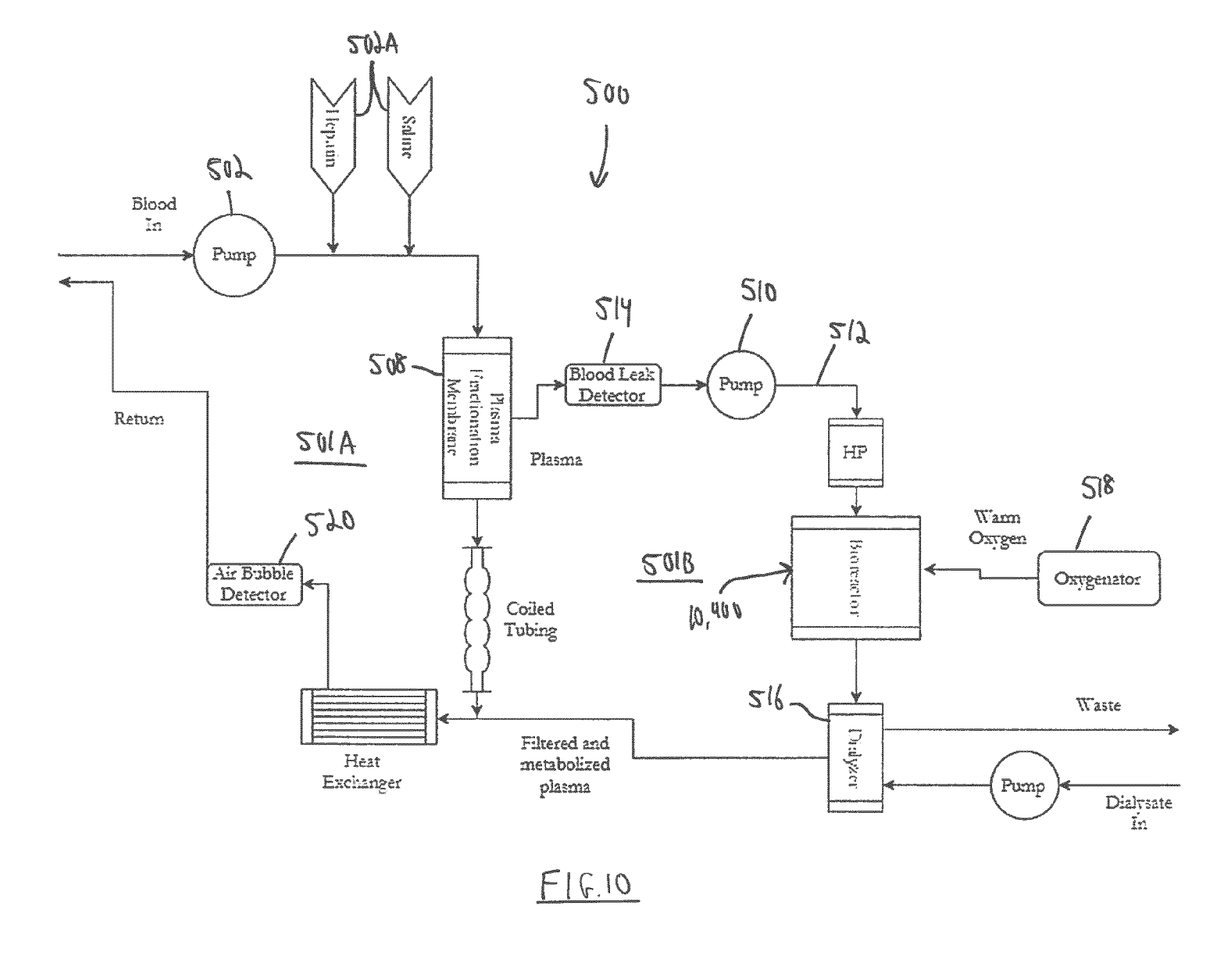
FIG. 10 is a schematic view of another artificial liver system having the perfusion bioreactor of FIG. 1A.

FIG. 10 shows another embodiment of an artificial liver system 500 having the bioreactor 10,400 described herein. The system 500 is a stand-alone extracorporeal unit which includes a blood circuit 501A and a plasma circuit 501B. The blood circuit 501A includes a pump 502 to pump blood into the system 500. Infusion pumps 502A are placed right after the pump 502 to insert saline and an anticoagulant (Heparin). A plasma fractionation module 508 separates the plasma from the blood, and provides the plasma to the plasma circuit 501B. In the plasma circuit 501B, the system 500 has a peristaltic pump 510 to circulate the plasma through the fluid network 512. A blood leak detector 514 is present upstream of the pump 510. The plasma circuit 501B also has an oxygenator 518 to dissolve oxygen into the plasma to produce oxygenated plasma. The bioreactor 10,400 is in fluid communication with the oxygenator 518, and receives the oxygenated plasma therefrom. The oxygenated plasma enters the bioreactor 10,400 and interacts with the ELTs 40 of the perfusion devices 20, which operate to diffuse remaining undesired solutes out of the oxygenated plasma and into the bodies 46 of the EOTs 40. The processed plasma exiting the housing outlet 18B of the bioreactor 10,400 is provided back to the blood circuit 501A, and then to the dialyzer 516, which removes some of the undesired solutes from the plasma using a dialysate. The treated plasma is recombined with the separated blood products and returned to the patient's blood, or further fluid processing may be performed. The blood circuit 501A has an air bubble detector 520 to prevent air from being introduced into the blood. The system 500 may also include temperature sensor(s), flow meter(s), a cell filter(s), heat exchanger(s) to maintain a constant temperature, clamp(s), drip chamber(s), and any other suitable devices. The system 500 may include a hemoperfusion (HP) cartridge, as shown in FIG. 10, which may be positioned upstream of the bioreactor 10,400.

Embodiments disclosed herein include:

A. A perfusion bioreactor, comprising: a housing having a length defined between a housing inlet and a housing outlet, the housing having an inner surface delimiting an internal cavity of the housing disposed between the housing inlet and the housing outlet and in fluid communication therewith; and perfusion devices disposed in the internal cavity of the housing, each of the perfusion devices comprising: a mesh structure supported from the inner surface of the housing, the mesh structure having a first wall spaced apart from a second wall to define an internal mesh cavity, each of the first and second walls of the mesh structure having openings therein to permit fluid communication through the mesh structure; and an encapsulated organ tissue disposed in the internal mesh cavity between the first and second walls of the mesh structure, the encapsulated organ tissue having at least one organoid at least partially covered with a biocompatible cross-linked polymer, the encapsulated organ tissue having a body with a thickness defined between a first surface of the body adjacent the first wall of the mesh structure and a second surface of the body adjacent the second wall of the mesh structure, the body having at least one channel extending into the body from one of the first and second surfaces to receive a fluid therein, the at least one channel having a diameter selected to diffuse solutes out of the fluid and into the body; the perfusion devices being disposed in the internal cavity of the housing one adjacent to another and spaced apart from each other along the length of the housing to receive the fluid conveyed from the housing inlet to the housing outlet, and to perfuse the fluid to the encapsulated organ tissue of each perfusion device and to the at least one channel therein.

B. A perfusion device, comprising: a mesh structure having a first wall spaced apart from a second wall to define an internal mesh cavity, each of the first and second walls of the mesh structure having openings therein to permit fluid communication through the mesh structure; and an encapsulated organ tissue disposed in the internal mesh cavity between the first and second walls of the mesh structure, the encapsulated organ tissue having at least one organoid at least partially covered with a biocompatible cross-linked polymer, the encapsulated organ tissue having a body with a thickness defined between a first surface of the body adjacent the first wall of the mesh structure and a second surface of the body adjacent the second wall of the mesh structure, the body having at least one channel extending into the body from one of the first and second surfaces to receive a fluid therein, the at least one channel having a diameter selected to diffuse solutes out of the fluid and into the body.

C. An artificial liver system, comprising: a fluid network and a pump to circulate plasma through the fluid network; and a perfusion bioreactor in fluid communication with the fluid network to receive the plasma therefrom, the perfusion bioreactor comprising: a housing having a length defined between a housing inlet and a housing outlet, the housing having an inner surface delimiting an internal cavity of the housing between the housing inlet and the housing outlet and in fluid communication therewith, the housing inlet receiving the plasma; and a plurality of perfusion devices disposed in the internal cavity of the housing, each of the perfusion devices comprising: a mesh structure supported from the inner surface of the housing, the mesh structure having a first wall spaced apart from a second wall to define an internal mesh cavity, each of the first and second walls of the mesh structure having openings therein to permit fluid communication through the mesh structure; and an encapsulated liver tissue disposed in the internal mesh cavity between the first and second walls of the mesh structure, the encapsulated liver tissue having at least one liver organoid at least partially covered with a biocompatible cross-linked polymer, the encapsulated liver tissue having a body with a thickness defined between a first surface of the body adjacent the first wall of the mesh structure and a second surface of the body adjacent the second wall of the mesh structure, the body having at least one channel extending into the body from one of the first and second surfaces to receive the plasma therein, the at least one channel having a diameter selected to diffuse undesired solutes out of the plasma and into the body; the perfusion devices being disposed in the internal cavity of the housing one adjacent to another and spaced apart from each other along the length of the housing to receive the plasma conveyed from the housing inlet to the housing outlet, and to perfuse the plasma to the encapsulated liver tissue of each perfusion device and to the at least one channel therein.

D. A method of processing blood plasma, comprising: conveying the blood plasma to at least one channel formed in an encapsulated liver tissue having at least one liver organoid at least partially covered with a biocompatible cross-linked polymer, the at least one channel having a diameter selected to diffuse undesired solutes out of the blood plasma and into the encapsulated liver tissue.

E. A method of making a perfusion device, comprising: providing at least one liver organoid at least partially covered with a biocompatible cross-linked polymer, the at least one liver organoid at least partially covered with the biocompatible cross-linked polymer having a body with at least one channel extending into the body, the at least one channel having a diameter selected to diffuse solutes out of a fluid and into the body; and positioning the body within a cavity of a mesh structure to allow the fluid to enter the cavity and the at least one channel of the body, and to exit the cavity.

Each of the embodiments A, B, C, D and E may have one or more of the following additional elements in any combination.

Element 1: the at least one channel of the body of each perfusion device extends through the body between the first and second surfaces.

Element 2: a length of the at least one channel is substantially equal to, or greater than, the thickness of the body.

Element 3: the at least one channel of one of the perfusion devices is offset from the at least one channel of an immediately adjacent perfusion device, the fluid following a winding flow path between the channels of the adjacent perfusion devices.

Element 4: the at least one channel of the body includes a first channel and at least another channel, the first channel extending through the body between the first and second surfaces, the at least another channel extending into the body from a first end at one of the first and second surfaces to a second end within the body at the first channel, the at least another channel being in fluid communication with the first channel.

Element 5: a length of the first channel is substantially equal to, or greater than, the thickness of the body, and a length of the at least another channel is less than or greater than the thickness of the body.

Element 6: the length of the at least another channel is greater than the thickness of the body.

Element 7: a plurality of supports spaced apart along the length of the housing, the mesh structure of each perfusion device being removably mounted to one of the supports.

Element 8: the housing has an upright orientation, the perfusion devices being supported from the housing one on top of another in a stack.

Element 9: the diameter of the at least one channel is between 150 µm and 750 µm.

Element 10: the at least one organoid of the encapsulated organ tissue includes a plurality of liver organoids.

Element 11: conveying the oxygenated blood plasma includes conveying the oxygenated blood plasma from the at least one channel to a second channel in another encapsulated liver tissue having at least one liver organoid at least partially covered with the biocompatible cross-linked polymer.

Element 12: conveying the oxygenated blood plasma includes conveying the oxygenated blood plasma from the at least one channel to a second channel in another encapsulated liver tissue having at least one liver organoid at least partially covered with the biocompatible cross-linked polymer, the second channel being misaligned with the at least one channel.

Element 13: conveying the oxygenated blood plasma from the at least one channel to the second channel includes conveying the oxygenated blood plasma to the second channel being vertically spaced apart from the at least one channel.

Element 14: cryopreserving the encapsulated liver tissue prior to conveying the blood plasma through the fluid network.

Element 15: warming the cryopreserved encapsulated liver tissue with the oxygenated blood plasma Element 16: providing the at least one liver organoid at least partially covered with the biocompatible cross-linked polymer includes forming the at least one channel in the body using photolithography.

Element 17: forming the at least one channel includes curing portions of the biocompatible cross-linked polymer with a UV light source while the body remains in the cavity of the mesh structure.

Element 18: forming the at least one channel includes injecting the at least one liver organoid and the biocompatible cross-linked polymer into the cavity of the mesh structure, and curing portions of the biocompatible cross-linked polymer with a UV light source.

Element 19: forming the at least one channel includes covering the body with a photomask having at least one opaque portion, and curing the biocompatible cross-linked polymer with a UV light source applied to the photomask, a portion of the body covered by the at least one opaque portion of the photomask remaining uncured to form the at least one channel.

Element 20: oxygenating the blood plasma to produce oxygenated blood plasma.

Element 21: oxygenating the blood plasma includes oxygenating the blood plasma before conveying the blood plasma to the at least one channel.

Element 22: oxygenating the blood plasma includes oxygenating the blood plasma in a perfusion bioreactor.

Element 23: an oxygenator in fluid communication with the fluid network to diffuse oxygen into the plasma to produce oxygenated plasma.

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure, and such modifications are intended to fall within the appended claims.

The invention claimed is:

1. A perfusion device, comprising:
 a mesh structure having a first wall spaced apart from a second wall to define an internal mesh cavity, each of the first and second walls of the mesh structure having openings therein to permit fluid communication through the mesh structure; and
 an encapsulated organ tissue disposed in the internal mesh cavity between the first and second walls of the mesh structure, the encapsulated organ tissue having at least one organoid at least partially covered with a biocompatible cross-linked polymer, the encapsulated organ tissue having a body with a thickness defined between a first surface of the body adjacent the first wall of the mesh structure and a second surface of the body adjacent the second wall of the mesh structure, the body having at least one channel extending into the body from one of the first and second surfaces to receive a fluid therein, the at least one channel having a diameter selected to diffuse solutes out of the fluid and into the body.

2. The perfusion device of claim 1, wherein the at least one channel of the body of each perfusion device extends through the body between the first and second surfaces.

3. The perfusion device of claim 2, wherein a length of the at least one channel is substantially equal to, or greater than, the thickness of the body.

4. The perfusion device of claim 1, wherein the at least one channel of the body includes a first channel and at least another channel, the first channel extending through the body between the first and second surfaces, the at least another channel extending into the body from a first end at one of the first and second surfaces to a second end within the body at the first channel, the at least another channel being in fluid communication with the first channel.

5. The perfusion device of claim 4, wherein a length of the first channel is substantially equal to, or greater than, the thickness of the body, and a length of the at least another channel is less than or greater than the thickness of the body.

6. The perfusion device of claim 5, wherein the length of the at least another channel is greater than the thickness of the body.

7. The perfusion device of claim 1, wherein the diameter of the at least one channel is between 150 μm and 750 μm.

8. The perfusion device of claim 1, wherein the at least one organoid of the encapsulated organ tissue includes a plurality of liver organoids.

9. An artificial liver system, comprising:
 a fluid network and a pump to circulate plasma through the fluid network; and
 a perfusion bioreactor in fluid communication with the fluid network to receive the plasma therefrom, the perfusion bioreactor comprising:
  a housing having a length defined between a housing inlet and a housing outlet, the housing having an inner surface delimiting an internal cavity of the housing between the housing inlet and the housing outlet and in fluid communication therewith, the housing inlet receiving the plasma; and
  a plurality of perfusion devices disposed in the internal cavity of the housing, each of the perfusion devices comprising:
   a mesh structure supported from the inner surface of the housing, the mesh structure having a first wall spaced apart from a second wall to define an internal mesh cavity, each of the first and second walls of the mesh structure having openings therein to permit fluid communication through the mesh structure; and
   an encapsulated liver tissue disposed in the internal mesh cavity between the first and second walls of the mesh structure, the encapsulated liver tissue having at least one liver organoid at least partially covered with a biocompatible cross-linked polymer, the encapsulated liver tissue having a body with a thickness defined between a first surface of the body adjacent the first wall of the mesh structure and a second surface of the body adjacent the second wall of the mesh structure, the body having at least one channel extending into the body from one of the first and second surfaces to receive the plasma therein, the at least one channel having a diameter selected to diffuse undesired solutes out of the plasma and into the body;

the perfusion devices being disposed in the internal cavity of the housing one adjacent to another and spaced apart from each other along the length of the housing to receive the plasma conveyed from the housing inlet to the housing outlet, and to perfuse the plasma to the encapsulated liver tissue of each perfusion device and to the at least one channel therein.

10. The artificial liver system of claim 9, wherein the at least one channel of the body of each perfusion device extends through the body between the first and second surfaces.

11. The artificial liver system of claim 10, wherein a length of the at least one channel is substantially equal to, or greater than, the thickness of the body.

12. The artificial liver system of claim 10, wherein the at least one channel of one of the perfusion devices is offset from the at least one channel of an immediately adjacent perfusion device, the fluid following a winding flow path between the channels of the adjacent perfusion devices.

13. The artificial liver system of claim 9, wherein the at least one channel of the body includes a first channel and at least another channel, the first channel extending through the body between the first and second surfaces, the at least another channel extending into the body from a first end at one of the first and second surfaces to a second end within the body at the first channel, the at least another channel being in fluid communication with the first channel.

14. The artificial liver system of claim 13, wherein a length of the first channel is substantially equal to, or greater than, the thickness of the body, and a length of the at least another channel is less than or greater than the thickness of the body.

15. The artificial liver system of claim 14, wherein the length of the at least another channel is greater than the thickness of the body.

16. The artificial liver system of claim 9, comprising a plurality of supports spaced apart along the length of the housing, the mesh structure of each perfusion device being removably mounted to one of the supports.

17. The artificial liver system of claim 9, wherein the housing has an upright orientation, the perfusion devices being supported from the housing one on top of another in a stack.

18. The artificial liver system of claim 9, wherein the diameter of the at least one channel is between 150 μm and 750 μm.

19. The artificial liver system of claim 9, wherein the at least one organoid of the encapsulated organ tissue includes a plurality of liver organoids.

20. The artificial liver system of claim 9, comprising an oxygenator in fluid communication with the fluid network to diffuse oxygen into the plasma to produce oxygenated plasma.

21. A method of processing blood plasma, comprising: conveying the blood plasma to at least one channel formed in an encapsulated liver tissue having at least one liver organoid at least partially covered with a biocompatible cross-linked polymer, the at least one channel having a diameter selected to diffuse undesired solutes out of the blood plasma and into the encapsulated liver tissue.

22. The method of claim 21, wherein conveying the blood plasma includes conveying the blood plasma from the at least one channel to a second channel in another encapsulated liver tissue having at least one liver organoid at least partially covered with the biocompatible cross-linked polymer.

23. The method of claim 21, wherein conveying the blood plasma includes conveying the blood plasma from the at least one channel to a second channel in another encapsulated liver tissue having at least one liver organoid at least partially covered with the biocompatible cross-linked polymer, the second channel being misaligned with the at least one channel.

24. The method of claim 22, wherein conveying the blood plasma from the at least one channel to the second channel includes conveying the blood plasma to the second channel being vertically spaced apart from the at least one channel.

25. The method of claim 21, comprising oxygenating the blood plasma to produce oxygenated blood plasma.

26. The method of claim 25, wherein oxygenating the blood plasma includes oxygenating the blood plasma before conveying the blood plasma to the at least one channel.

27. The method of claim 25, wherein oxygenating the blood plasma includes oxygenating the blood plasma in a perfusion bioreactor.

* * * * *